(12) United States Patent
Fife et al.

(10) Patent No.: US 8,963,216 B2
(45) Date of Patent: *Feb. 24, 2015

(54) CHEMICAL SENSOR WITH SIDEWALL SPACER SENSOR SURFACE

(71) Applicant: Life Technologies Corporation, Carlsbad, CA (US)

(72) Inventors: Keith Fife, Palo Alto, CA (US); James Bustillo, Castro Valley, CA (US); Jordan Owens, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/801,002

(22) Filed: Mar. 13, 2013

(65) Prior Publication Data

US 2014/0264464 A1     Sep. 18, 2014

(51) Int. Cl.
G01N 27/414     (2006.01)

(52) U.S. Cl.
CPC .................................. *G01N 27/4145* (2013.01)
USPC .......................................... 257/253; 438/49

(58) Field of Classification Search
CPC .................................................... G01N 27/414
USPC .......................................... 257/253; 438/49
See application file for complete search history.

(56) References Cited

U.S. PATENT DOCUMENTS

| 4,086,642 A | 4/1978 | Yoshida et al. |
| 4,411,741 A | 10/1983 | Janata |
| 4,490,678 A | 12/1984 | Kuisl et al. |
| 4,641,084 A | 2/1987 | Komatsu |
| 4,691,167 A | 9/1987 | Vlekkert et al. |
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau |

(Continued)

FOREIGN PATENT DOCUMENTS

| CN | 1582334 | 2/2005 |
| CN | 1585896 | 2/2005 |

(Continued)

OTHER PUBLICATIONS

Bockelmann, U. et al., "Detecting DNA by field effect transistor arrays", *Proceedings of the 2006 IFIP International Conference on Very Large Scale Integration*, 2006, 164-168.

(Continued)

*Primary Examiner* — Marc Armand

(57) ABSTRACT

In one implementation, a chemical sensor is described. The chemical sensor includes chemically-sensitive field effect transistor including a floating gate conductor having an upper surface. A dielectric material defines an opening extending to the upper surface of the floating gate conductor. A conductive sidewall spacer is on a sidewall of the opening and contacts the upper surface of the floating gate conductor.

10 Claims, 8 Drawing Sheets

(56) References Cited

U.S. PATENT DOCUMENTS

| | | |
|---|---|---|
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,624,637 B1 | 9/2003 | Pechstein et al. |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,682,899 B2 | 1/2004 | Bryan et al. |
| 6,682,936 B2 | 1/2004 | Kovacs |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B1 | 8/2006 | Zenhausern |
| 7,105,300 B2 | 9/2006 | Parce et al. |
| 7,129,554 B2 | 10/2006 | Lieber et al. |
| 7,169,560 B2 | 1/2007 | Lapidus et al. |
| 7,190,026 B2 | 3/2007 | Lotfi |
| 7,192,745 B2 | 3/2007 | Jaeger |
| 7,193,453 B2 | 3/2007 | Wei et al. |
| 7,211,390 B2 | 5/2007 | Rothberg et al. |
| 7,220,550 B2 | 5/2007 | Keen |
| 7,223,540 B2 | 5/2007 | Pourmand et al. |
| 7,226,734 B2 | 6/2007 | Chee et al. |
| 7,229,799 B2 | 6/2007 | Williams et al. |
| 7,235,389 B2 | 6/2007 | Lim et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |

(56) References Cited

U.S. PATENT DOCUMENTS

| | | |
|---|---|---|
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee et al. |
| 7,612,369 B2 | 11/2009 | Stasiak |
| 7,612,817 B2 | 11/2009 | Tay |
| 7,614,135 B2 | 11/2009 | Santini et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,114,591 B2 | 2/2012 | Toumazou et al. |
| 8,124,936 B1 | 2/2012 | Lagna |
| 8,133,698 B2 | 3/2012 | Silver et al. |
| 8,138,496 B2 | 3/2012 | Li et al. |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,582 B2 | 7/2012 | Sauer et al. |
| 8,232,813 B2 | 7/2012 | Burdett et al. |
| 8,247,849 B2 | 8/2012 | Fife et al. |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,343,856 B2 | 1/2013 | Therrien et al. |
| 8,349,167 B2 | 1/2013 | Rothberg et al. |
| 8,361,713 B2 | 1/2013 | Bridgham et al. |
| 8,383,396 B2 | 2/2013 | Kamahori et al. |
| 8,426,898 B2 | 4/2013 | Rothberg et al. |
| 8,445,194 B2 | 5/2013 | Drmanac et al. |
| 8,449,824 B2 | 5/2013 | Sun |
| 8,552,771 B1 | 10/2013 | Jordan et al. |
| 8,558,288 B2 | 10/2013 | Rothberg et al. |
| 8,592,154 B2 | 11/2013 | Rearick et al. |
| 8,673,627 B2 | 3/2014 | Nobile et al. |
| 8,841,217 B1* | 9/2014 | Fife et al. .................. 438/700 |
| 2002/0012933 A1 | 1/2002 | Rothberg et al. |
| 2002/0042388 A1 | 4/2002 | Cooper et al. |
| 2002/0150909 A1 | 10/2002 | Stuelpnagel et al. |
| 2002/0168678 A1 | 11/2002 | Williams et al. |
| 2003/0054396 A1 | 3/2003 | Weiner |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0152930 A1 | 8/2003 | Howard |
| 2003/0155942 A1 | 8/2003 | Thewes et al. |
| 2003/0186262 A1 | 10/2003 | Cailloux et al. |
| 2003/0211502 A1 | 11/2003 | Sauers et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0136866 A1 | 7/2004 | Pontis et al. |
| 2004/0185484 A1 | 9/2004 | Costa et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0106587 A1 | 5/2005 | Klapproth et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0202582 A1 | 9/2005 | Eversmann et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0233318 A1 | 10/2005 | Chee et al. |
| 2005/0239132 A1 | 10/2005 | Klapproth |
| 2005/0282224 A1 | 12/2005 | Fouillet et al. |
| 2006/0000772 A1 | 1/2006 | Sano et al. |
| 2006/0024711 A1 | 2/2006 | Lapidus et al. |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0141474 A1 | 6/2006 | Miyahara et al. |
| 2006/0166203 A1 | 7/2006 | Tooke et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2007/0069291 A1 | 3/2007 | Stuber et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0212681 A1 | 9/2007 | Shapiro et al. |
| 2007/0231824 A1 | 10/2007 | Chee et al. |
| 2007/0233477 A1 | 10/2007 | Halowani et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0096216 A1 | 4/2008 | Quake |
| 2008/0121946 A1 | 5/2008 | Youn et al. |
| 2008/0185616 A1 | 8/2008 | Johnson et al. |
| 2008/0205559 A1 | 8/2008 | Iida |
| 2008/0210931 A1 | 9/2008 | Truong et al. |
| 2008/0230386 A1 | 9/2008 | Srinivasan et al. |

(56) References Cited

U.S. PATENT DOCUMENTS

| | | |
|---|---|---|
| 2009/0026082 A1 | 1/2009 | Rothberg et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0120905 A1 | 5/2009 | Kohl et al. |
| 2009/0127589 A1 | 5/2009 | Rothberg et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2010/0007326 A1 | 1/2010 | Nakazato |
| 2010/0137143 A1 | 6/2010 | Rothberg et al. |
| 2010/0244106 A1 | 9/2010 | Parker et al. |
| 2010/0273166 A1 | 10/2010 | Garcia |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001646 A1 | 1/2012 | Bolander et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife et al. |
| 2012/0074956 A1 | 3/2012 | Fife et al. |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0161207 A1 | 6/2012 | Homyk et al. |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| CN | 1826525 | 8/2006 |
| CN | 102203282 | 9/2011 |
| DE | 102008012899 | 9/2009 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 2002272463 | 9/2002 |
| JP | 2005218310 | 8/2004 |
| JP | 05077210 | 3/2005 |
| JP | 2005518541 | 6/2005 |
| JP | 06138846 | 6/2006 |
| JP | 2011525810 | 9/2011 |
| KR | 100442838 | 7/2004 |
| KR | 100455283 | 10/2004 |
| WF | WO2004040291 | 5/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/81896 | 11/2001 |
| WO | WO-02/077287 | 10/2002 |
| WO | WO-02/086162 | 10/2002 |
| WO | WO-03/073088 | 9/2003 |
| WO | WO-2004/040291 | 5/2004 |
| WO | WO2004048962 | 6/2004 |
| WO | WO2005015156 | 2/2005 |
| WO | WO-2005/047878 | 5/2005 |
| WO | WO2005043160 | 5/2005 |
| WO | WO-2005/054431 | 6/2005 |
| WO | WO2005602049 | 7/2005 |
| WO | WO-2005/084367 | 9/2005 |
| WO | WO2005090961 | 9/2005 |
| WO | WO-2006/005967 | 1/2006 |
| WO | WO-2006/022370 | 3/2006 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | WO2009041917 | 4/2009 |
| WO | WO2009074926 | 6/2009 |
| WO | WO2009081890 | 7/2009 |
| WO | WO-2009/158006 | 12/2009 |
| WO | WO-2010/008480 | 1/2010 |
| WO | WO-2010/047804 | 4/2010 |
| WO | WO-2010/138182 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |
| WO | WO2012003359 | 1/2012 |

OTHER PUBLICATIONS

EP11801439.8 EP Extended Search Report dated Mar. 7, 2014.
Tokuda, T. et al., "A CMOS image sensor with optical and potential dual imaging function for on-chip bioscientific applications", *Sensors and Actuators A*, vol. 125, No. 2, 2006, 273-280.
EP14152861.2 EP Search Report date Jul. 7, 2014.

(56) References Cited

OTHER PUBLICATIONS

Palan, B. et al., "New ISFET sensor interface circuit for biomedical applications", Sensors and Actuators B: Chemical: International Journal Devoted to Research and Development of Physical and Chemical Transducers, Elsevier S.A. Ch., vol. 57, No. 1-3, 1999, pp. 63-68.
PCT/US2013/022129 International Preliminary Report on Patentability dated Jul. 22, 2014.
PCT/US2013/022140 International Preliminary Report on Patentability dated Jul. 22, 2014.
Zhao, B. et al., "Floating-Gate Ion Sensitive Field-Effect Transistor for Chemical and Biological Sensing", MRS Proceedings, vol. 828, 2004, pp. 349-354.
Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP11801437.2 Extended European Search Report dated Jul. 25, 2013.
EP11804218.3 Extended European Search Report dated Jul. 11, 2013.
EP11804218.3 First Office Action dated Jul. 29, 2013.
EP11827128.7 European Search Report dated Aug. 1, 2013.
EP13161312.7 Extended European Search Report dated Oct. 15, 2013.
EP13163995.7 Extended European Search Report dated Aug. 20, 2013.
Eriksson, J. et al. "Pyrosequencing Technology at Elevated Temperature" Electrophoresis, vol. 25, 2004, pp. 20-27.
Hanshaw, R. et al., "An indicator displacement system for fluorescent detection of phosphate oxyanions under physiological conditions" Science Direct, Tetrahedron Ltrs., vol. 45, 2004, pp. 8721-8724.
Hizawa, et al. "Sensing Characteristics of Charge Transfer Type pH Sensor by Accumulative Operation" IEEE Sensors, EXCO, Daegu, Korea, 2006, pp. 144-147.
JP20120246413 First Office Action dated Jun. 28, 2013.
Lee, S. et al. "An Enhanced Glucose Biosensor Using Charge Transfer Techniques" Biosensors and Bioelectronics, vol. 24, 2008, pp. 650-656.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-2255.
PCT/US2011/042683 International Preliminary Report on Patentability Mailed Jun. 4, 2013.
PCT/US2013/022129 International Search Report and Written Opinion dated Aug. 9, 2013.
Premanode, B. et al. "Drift Reduction in Ion-Sensitive FETs Using Correlated Double Sampling", Electronics Letters, IEEE Stevenage, GB, vol. 43 (16) Aug. 2, 2007.
Rothberg, J. et al., "An integrated semiconductor device enabling non-optical genome sequencing" Nature, vol. 475, No. 7356, 2011, pp. 348-352.
Sawada, K. et al., "Highly sensitive ion sensors using charge transfer technique", Sensors Actuators B, vol. 98, 2004, pp. 69-72.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
EP13174555.6 EP Extended Search Report Dec. 12, 2013.
EP13174555.6 EP Search Report Nov. 21, 2013.
EP13177039.8 EP Search Report Nov. 21, 2013.
EP13177590.0 EP Search Report Nov. 20, 2013.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Wood, et al. "Base composition-independent hybridization in tetramethylammonium chloride: a method for oligonucleotide screening of highly complex gene libraries" Proc. Nat. Acad. Sci., 1985, pp. 1585-1588.
[No Author Listed], "ISFET Wikipedia article", Wikipedia, Last modified Nov. 7, 2006.
Akiyama, T. et al., "Ion-Sensitive Field-Effect Transistors with Inorganic Gate Oxide for pH Sensing", IEE Transactions on Electron Devices, vol. ED-29 (12), 1982, pp. 1936-1941.
AU2011226767 Search Information Statement Mailed Oct. 26, 2011.
Bandiera, L. et al., "A fully electronic sensor for the measurement of cDNA hybridization kinetics", Biosens Bioelectron, vol. 22, 2007, pp. 2108-2114.
Barbaro, M. et al., "A CMOS, Fully Integrated Sensor for Electronic Detection of DNA Hybridization", IEEE Electron Device Letters, vol. 27(7), 2006, pp. 595-597.
Barbaro, M. et al., "A Charge-Modulated FET for Detection of Biomolecular Processes: Conception, Modeling, and Simulation", IEEE Transactions on Electron Devices, vol. 53(1), 2006, pp. 158-166.
Barbaro, M. et al., "Fully electronic DNA hybridization detection by a standard CMOS biochip", Sensors and Actuators B Chemical, vol. 118, 2006, pp. 41-46.
Bashford, G. et al., "Automated bead-trapping apparatus and control system for single-molecule DNA sequencing", Optics Express, vol. 16(5), 2008, pp. 3445-3455.
Baumann, W. et al., "Microelectronic sensor system for microphysiological application on living cells", Sensors and Actuators B, vol. 55(1), 1999, pp. 77-89.
Bausells, J. et al., "Ion-sensitive field-effect transistors fabricated in a commercial CMOS technology", Sensors and Actuators B Chemical, vol. 57(1-3), 1999, pp. 56-62.
Bergveld, P., "ISFET, Theory and Practice", IEEE Sensor Conference, Toronto, Oct. 2003, 2003, pp. 1-26.
Bergveld, P., "Thirty years of ISFETOLOGY What happened in the past 30 years and what may happen in the next 30 years", Sensors and Actuators B, vol. 88(1), 2003, pp. 1-20.
Besselink, G. et al., "ISFET Affinity Sensor", Methods in Biotechnology, vol. 7: Affinity Biosensors: Techniques and Protocols, 1998, pp. 173-185.
Bobrov, P. et al., "Chemical sensitivity of an ISFET with $Ta_2O_5$ membrane in strong acid and alkaline solutions", Sensors and Actuators B, vol. 3, 1991, pp. 75-81.
Bousse, L. et al., "A process for the combined fabrication of ion sensors and CMOS circuits", IEEE Electron Device Letters, vol. 9(1), 1988, pp. 44-46.
Bousse, L. et al., "Zeta potential measurements of $Ta_2O_5$ and $SiO_2$ thin films", J. Colloid Interface Sci., vol. 147(1), 1991, pp. 22-32.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chen, Y. et al., "Nanoscale field effect transistor for biomolecular signal amplification", App Phys Letter, vol. 91(24), 2007, pp. 243511-1-243511-3.
Chen, Y. et al., "Silicon-based nanoelectronic field-effect pH sensor with local gate control", App Phys Letter, vol. 89, 2006, pp. 223512-1-223512-3.
Chinese Patent Application 200780051353.2 Second Office Action Mailed Mar. 5, 2013.
Chou, J. et al., "Letter to the Editor on Simulation of Ta2O5 gate ISFET temperature characteristics", Sensors and Actuators B, vol. 80, 2001, pp. 290-291.
Chou, J. et al., "Simulation of Ta2O5 gate ISFET temperature characteristics", Sensor and Actuators B, vol. 71, Letter to the Editor, 2000, pp. 73-76.
Chung, W-Y. et al., "ISFET interface circuit embedded with noise rejection capability", Electronics Letters, vol. 40(18), e-pub, 2004, 1115-1116.

(56) References Cited

OTHER PUBLICATIONS

Chung, W-Y. et al., "ISFET performance enhancement by using the improved circuit techniques", Sensors and Actuators B, vol. 113, 2006, pp. 555-562.
Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
Eijkel, J. et al., "Measuring Donnan-related phenomena using a solid-state ion sensor and a concentration-step method", J. Membrane Sci., vol. 127, 1997, pp. 203-221.
Eijkel, J., "Potentiometric detection and characterization of adsorbed protein using stimulus-response measurement techniques", Thesis, Sep. 3, 1955, pp. 1-147; 160-192.
Eltoukhy, H. et al., "A 0.18um CMOS 10-6 lux Bioluminescence Detection System-on-Chip", ISSCC 2004/Session12/Biomicrosystems/12.3, 2004, pp. 1-3.
Eltoukhy, H. et al., "A. 0.18-um CMOS Bioluminescence Detection Lab-on-Chip", IEEE J Solid-State Circuits, vol. 41(3), 2006, pp. 651-662.
EP7867780.4 Examination Report Mailed Jul. 3, 2012.
Esfandyarpour, H. et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Eversmann, B. et al., "A 128×128 CMOS Biosensor Array for Extracellular Recording of Neural Activity", IEEE J. Solid-State Circ., vol. 38(12), 2003, pp. 2306-2317.
Faramarzpour, N. et al., "CMOS-Based Active Pixel for Low-Light Level Detection: Analysis and Measurements", IEEE Trans Electron Devices, vol. 54(12), 2007, pp. 3229-3237.
Finn, A. et al., "Towards an Optimization of FET-Based Bio-Sensors", European Cells and Materials, vol. 4, Sup 2, 2002, pp. 21-23.
Fraden, J., "Handbook of Modern Sensors-Physics, Designs, and Applications", 17.3.2 CHEMFET Sensors, 1996, pp. 499-501.
Fritz, J. et al., "Electronic detection of DNA by its intrinsic molecular charge", PNAS, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", Proc IEEE 1992 Intl Conf Microelec Test Struct, 1992, pp. 156-159.
Hammond, P. et al., "A System-on-Chip Digital pH Meter for Use in a Wireless Diagnostic Capsule", IEEE Trans Biomedical Eng., vol. 52(4), 2005, pp. 687-694.
Hammond, P. et al., "Design of a Single-Chip pH Sensor Using a Conventional 0.6-µm CMOS Process", IEEE Sensors Journal, vol. 4(6), 2004, pp. 706-712.
Hammond, P. et al., "Encapsulation of a liquid-sensing microchip using SU-8 photoresist", MicoElectronic Engineering, vol. 73-74, 2004, pp. 893-897.
Hammond, S. et al., "Genomic sequencing and analysis of a Chinese Hamster ovary cell line using Illumina sequencing technology", BMC Genomics, vol. 12:67, 2011, pp. 1-8.
Han, Y., "Label-free detection of biomolecules by a field-effect transistor microarray biosensor with bio-functionalized gate surfaces", Aachen, Techn. Hochsch., Diss., 2006, pp. 1-63.
Hara, H. et al., "Dynamic response of a $Ta_2O_5$-gate pH-sensitive field-effect transistor", Sensors Actuators B, vol. 32, 1996, pp. 115-119.
Hermon, Z. et al., "Miniaturized bio-electronic hybrid for chemical sensing applications", Tech Connect News, 2008, p. 1.
Hideshima, S. et al., "Detection of tumor marker in blood serum using antibody-modified field effect transistor with optimized BSA blocking", Sensors and Actuations B: Chemical, vol. 161, 2012, pp. 146-150.

Hizawa, T. et al., "Fabrication of a two-dimensional pH image sensor using a charge transfer technique", Sensors and Actuators B Chemical, vol. 117, 2006, pp. 509-515.
Hizawa, T. et al., "32×32 pH Image Sensors for Real Time Observation of Biochemical Phenomena", Solid-State Sensors, Actuators and Microsystems Conference, 2007, Transducers 2007. International, 2007, pp. 1311-1312.
Jakobson, C. et al., "Low frequency noise and drift in Ion Sensitive Field Effect Transistors", Sensors Actuators B, vol. 68, 2000, pp. 134-139.
Ji, H. et al., "A CMOS contact imager for locating individual cells", ISCAS, 2006, pp. 3357-3360.
Ji, H. et al., "Contact Imaging: Simulation and Experiment", IEEE Trans Circuits Systems-I: Regular Papers, vol. 54(8), 2007, pp. 1698-1710.
Kim, D. et al., "An FET-type charger sensor for highly sensitive detection of DNA sequence", Biosens Bioelectron, vol. 20(1), 2004, pp. 69-74.
Klein, M., "Time effects of ion-sensitive field-effect transistors", Sensors and Actuators B, vol. 17(1-2), 1989, pp. 203-208.
Koch, S. et al., "Protein detection with a novel ISFET-based zeta potential analyzer", Biosensors & Bioelectronics, vol. 14, 1999, pp. 413-421.
Krause, M. et al., "Extended Gate Electrode Arrays for Extracellular Signal Recordings", Sensors and Actuators B, vol. 70, 2000, pp. 101-107.
Kruise, J. et al., "Detection of protein concentrations using a pH-step titration method", Sensors Actuators B, vol. 44, 1997, pp. 297-303.
Leamon, J. et al., "A Massively Parallel PicoTiterPlate Based Platform for Discrete Picoliter-Scale Polymerase Chain Reactions", Electrophoresis, vol. 24, 2003, pp. 3769-3777.
Leamon, J. et al., "Cramming More Sequencing Reactions onto Microreactor Chips", Chemical Reviews, vol. 107, 2007, pp. 3367-3376.
Lee, C-S. et al., "Ion-sensitive Field-Effect Transistor for Biological Sensing", Sensors, vol. 9, 2009, pp. 7111-7131.
Lohrengel, M. et al., "A new microcell or microreactor for material surface investigations at large current densities", Electrochimica Acta, vol. 49, 2004, pp. 2863-2870.
Lui, A. et al., "A Test Chip for ISFET/CMNOS Technology Development", Proc. of the 1996 IEEE Intl. Conf. on Microelectronic Test Structures, vol. 9, 1996, pp. 123-128.
Margulies, M. et al., "Genome sequencing in microfabricated high-density picolitre reactors", Nature, vol. 437(7057), 2005, pp. 376-380.
Marshall, A. et al., "DNA chips: an array of possibilities", Nature Biotechnology, vol. 16, 1998, pp. 27-31.
Martinoia, S. et al., "A behavioral macromodel of the ISFET in SPICE", Sensors Actuators B, vol. 62, 2000, pp. 182-189.
Martinoia, S. et al., "Development of ISFET Array-Based Microsystems for Bioelectrochemical measurements of cell populations", Biosensors & Bioelectronics, vol. 16, 2001, pp. 1043-1050.
Medoro, G. et al., "A Lab-on-a-Chip for Cell Detection and Manipulation", IEEE Sensors J, vol. 3(3), 2003, pp. 317-325.
Meyburg, S. et al., "N-Channel field-effect transistors with floating gates for extracellular recordings", Biosens Bioelectron, vol. 21(7), 2006, pp. 1037-1044.
Milgrew, M. et al., "A 16×16 CMOS proton camera array for direct extracellular imaging of hydrogen-ion activity", IEEE Intl Solid-State Circuits Conf, Session 32:24, 2008, pp. 590-638.
Milgrew, M. et al., "A large transistor based sensor array chip for direct extracellular imaging", Sensors and Actuators B Chemical, vol. 111-112, 2005, pp. 347-353.
Milgrew, M. et al., "Matching the transconductance characteristics of CMOS ESFET arrays by removing trapped charge", IEEE Trans Electron Devices, vol. 55(4), 2008, pp. 1074-1079.
Milgrew, M. et al., "Microsensor Array Technology for Direct Extracellular Imaging", Dept Electronic and EE, University of Glasgow, 2006, pp. 1-23.
Milgrew, M. et al., "The development of scalable sensor arrays using standard CMOS technology", Sensors and Actuators B, vol. 103, 2004, pp. 37-42.

(56) References Cited

OTHER PUBLICATIONS

Milgrew, M. et al., "The fabrication of scalable multi-sensor arrays using standard CMOS technology", 2003 IEEE Custom Integrated Circuits Conference, 2003, pp. 513-516.
Miyahara, Y. et al., "Biochip Using Micromachining Technology", J. Institute of Electrostatics, Japan, vol. 27(6), (Translation Included), 2003, pp. 268-272.
Miyahara, Y. et al., "Direct Transduction of Primer Extension into Electrical Signal Using Genetic Field Effect Transistor", Micro Total Analysis Systems 2004, vol. 1, 2004, pp. 303-305.
Miyahara, Y. et al., "Potentiometric Detection of DNA Molecules Using Field Effect Transistor", The Japan Society of Applied Physics, No. 3 (Translation included), 2003, pp. 1180.
Nyren, P. et al., "Enzymatic Method for Continuous Monitoring of Inorganic Pyrophosphate Synthesis", Analytical Biochemistry, vol. 151, 1985, pp. 504-509.
Oelbner, W. et al., "Encapsulation of ESFET sensor chips", Sensors Actuators B, vol. 105, 2005, pp. 104-117.
Oelbner, W. et al., "Investigation of the dynamic response behaviour of ISFET pH sensors by means of laser Doppler velocimetry (LDV)", Sensors Actuators B, vol. 26-27, 1995, pp. 345-348.
Offenhausser, A. et al., "Field-Effect transistor array for monitoring electrical activity from mammalian neurons in culture", Biosensors & Bioelectronics, vol. 12(8), 1997, pp. 819-826.
Ohno, Y. et al., "Electrolyte-Gated Graphene Field-Effect Transistors for Detecting pH and Protein Adsorption", Nano Letters, vol. 9(9), Jul. 28, 2009, pp. 3318-3322.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
Patolsky, F. et al., "Nanowire-Based Biosensors", Analyt Chem 1, vol. 78(13), 2006, pp. 4261-4269.
PCT/US2009/05745 International Preliminary Report on Patentability Mailed Apr. 26, 2011.
PCT/US2009/05745 International Search Report Mailed Dec. 11, 2009.
PCT/US2009/05745 Written Opinion Mailed Dec. 11, 2009.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011.
PCT/US2010/001543 International Search Report and Written Opinion Mailed Oct. 13, 2010.
PCT/US2010/048835 International Preliminary Report on Patentability Mailed Mar. 19, 2013.
PCT/US2010/048835 International Search Report and Written Opinion Mailed Dec. 16, 2010.
PCT/US2011/042655 International Search Report Mailed Oct. 21, 2011.
PCT/US2011/042660 International Search Report Mailed Nov. 2, 2011.
PCT/US2011/042665 International Search Report Mailed Nov. 2, 2011.
PCT/US2011/042668 International Preliminary Report on Patentability Mailed Mar. 26, 2013.
PCT/US2011/042668 International Search Report Mailed Oct. 28, 2011.
PCT/US2011/042669 International Search Report Mailed Jan. 9, 2012.
PCT/US2011/042669 Written Opinion Mailed Jan. 9, 2012.
PCT/US2011/042683 International Search Report Mailed Feb. 16, 2012.
PCT/US2011/042683 Written Opinion Mailed Feb. 16, 2012.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.
Poghossian, A. et al., "Functional testing and characterization of ISFETs on wafer level by means of a micro-droplet cell", Sensors, vol. 6, 2006, pp. 397-404.
Pollack, J. et al., "Genome-Wide Analysis of DNA copy-number changes using cDNA Microarrays", Nature Genetics, vol. 23, 1999, pp. 41-46.
Pourmand, N. et al., "Direct electrical detection of DNA synthesis", PNAS, vol. 103(17), 2006, pp. 6466-6470.
Pouthas, F. et al., "Spatially resolved electronic detection of biopolymers", Phys Rev, vol. 70, 2004, pp. 031906-1-031906-8.
Premanode, B. et al., "A composite ISFED readout circuit employing current feedback", Sensors Actuators B, vol. 127, 2007, pp. 486-490.
Premanode, B. et al., "A novel, low power biosensor for real time monitoring of creatine and urea in peritoneal dialysis", Sensors Actuators B, vol. 120, 2007, pp. 732-735.
Premanode, B. et al., "Ultra-low power precision ISFET readout using global current feedback", Electronic Lett, vol. 42(22), 2006, pp. 1264-1265.
Purushothaman, S. et al., "Protons and single nucleotide polymorphism detection: A simple use for the Ion Sensitive Field Effect Transistor", Sensors and Actuators B Chemical, vol. 114(2), 2006, pp. 964-968.
Purushothaman, S. et al., "Towards Fast Solid State DNA Sequencing", IEEE ISCAS 2002 Proceedings, Circuits and Systems, vol. 4, 2002, pp. IV-169-IV-172.
Rodriguez-Villegas, E., "Solution to trapped charge in FGMOS transistors", Electronics Letters, vol. 39(19), 2003.
Sakata, T. et al., "Cell-based field effect devices for cell adhesion analysis", Intl. Conf. on Microtechnologies in Medicine and Biology, May 9-12, 2006, Okinawa, Japan, pp. 177-179.
Sakata, T. et al., "Detection of DNA recognition events using multi-well field effect transistor", Biosensors and Bioelectronics vol. 21, 2005, pp. 827-832.
Sakata, T. et al., "Detection sensitivity of genetic field effect transistor combined with charged nanoparticle-DNA conjugate", Proc. of 2006 Intl. Conf. on Microtechnologies in Medicine and Biology, May 9-12, 2006, Okinawa, Japan, pp. 97-100.
Sakata, T. et al., "Direct detection of single nucleotide polymorphism using genetic field effect transistor", Digest of Papers Microprocesses and Nanotechnology 2004, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.
Sakata, T. et al., "Direct transduction of allele-specific primer extension into electrical signal using genetic field effect transistor", Biosensors and Bioelectronics, vol. 22, 2007, pp. 1311-1316.
Sakata, T. et al., "DNA Analysis Chip Based on Field-Effect Transistors", Japanese Journal of Applied Physics, vol. 44(4B), 2005, pp. 2854-2859.
Sakata, T. et al., "DNA Sequencing Based on Intrinsic Molecular Charges", Angewandte Chemie International Edition 2006, vol. 118, 2006, pp. 2283-2286.
Sakata, T. et al., "DNA Sequencing Based on Intrinsic Molecular Charges", Angewandte Chemie International Edition 2006, vol. 45, 2006, pp. 2225-2228.
Sakata, T. et al., "DNA Sequencing Using Genetic Field Effect Transistor", Solid-State Sensors, Actuators and Microsystems, vol. 2, 2005, pp. 1676-1679.

(56) References Cited

OTHER PUBLICATIONS

Sakata, T. et al., "Immobilization of oligonucleotide probes on Si3N4 surface and its application to genetic field effect transistor", Materials Science and Engineering: C, vol. 24, 2004, pp. 827-832.

Sakata, T. et al., "Potential Behavior of Biochemically Modified Gold Electrode for Extended-Gate Field-Effect Transistor", Japanese Journal of Applied Physics, vol. 44(4B), 2005, pp. 2860-2863.

Sakata, T. et al., "Potential Response of Genetic Field Effect Transistor to Charged Nanoparticle-DNA Conjugate", Digest of Papers Microprocesses and Nanotechnology 2005, Tokyo, Japan, 2005 Intl Microprocesses and Nanotech Conf., Hotel Bellclassic, 2005, pp. 42-43.

Sakata, T. et al., "Potentiometric Detection of Allele Specific Oligonucleotide Hybridization Using Genetic Field Effect Transistor", Micro Total Analysis Systems, 8th Intl. Conf. on Miniaturized Systems for Chemistry and Life Sciences, 2004, pp. 300-302.

Sakata, T. et al., "Potentiometric detection of DNA molecules hybridization using gene field effect transistor and intercalator" Materials Research Society Symposium Proceedings, vol. 782, 2004, pp. 393-400.

Sakata, T. et al., "Potentiometric Detection of DNA Using Genetic Transistor", Denki Gakkai Kenkyukai Shiryo Chemical Sensor Kenkyukai, CHS-03-51-55, 2003, pp. 1-5.

Sakata, T. et al., "Potentiometric Detection of Single Nucleotide Polymorphism by Using a Genetic Field-effect transistor", ChemBioChem, vol. 6, 2005, pp. 703-710.

Sakurai, T. et al., "Real-Time Monitoring of DNA Polymerase Reactions by a Micro ISFET pH Sensor", Anal Chem, vol. 64(17), 1992, pp. 1996-1997.

Salama, K., "CMOS luminescence detection lab-on-chip: modeling, design, and characterization", Thesis, Presented at Stanford University, 2005, pp. ii-78.

Salama, K., "Modeling and simulation of luminescence detection platforms", Biosensors & Bioelectronics, 2004, pp. 1377-1386.

Sawada, K. et al., "A novel fused sensor for photo- and ion-sensing", Sensors Actuators B, vol. 106, 2005, pp. 614-618.

Schasfoort, R. et al., "A new approach to immunoFET operation", Biosensors & Bioelectronics, vol. 5, 1990, pp. 103-124.

Schasfoort, R. et al., "Field-effect flow control for microfabricated fluidic networks", Science, vol. 286(5441), 1999, pp. 942-945.

Schoning, M. et al., "Bio FEDs (Field-Effect Devices): State-of-the-Art and New Directions", Electroanalysis, vol. 18(19-20), 2006, pp. 1893-1900.

SG200903992-6 Search and Examination Report Mailed Jan. 20, 2011.

Shah, N., "Microfabrication of a parellel-array DNA pyrosequencing chip", NNIN REU Research Accomplishments, 2005, pp. 130-131.

Shepherd, L. et al., "A biochemical translinear principle with weak inversion ISFETs", IEEE Trans Circuits Syst-I, vol. 52(12), 2005, pp. 2614-2619.

Shepherd, L. et al., "A novel voltage-clamped CMOS ISFET sensor interface", IEEE, 2007, pp. 3331-3334.

Shepherd, L. et al., "Towards direct biochemical analysis with weak inversion ISFETS", Intl Workshop on Biomedical, 2004, S1.5-5-S1.5-8.

Shepherd, L. et al., "Weak inversion ISFETs for ultra-low power biochemical sensing and real-time analysis", Sensors Actuators B, vol. 107, 2005, pp. 468-473.

Shi, Y. et al., "Radical Capillary Array Electrophoresis Microplace and Scanner for High-Performance Nucleic Acid Analysis", Anal. Chem., vol. 71(23), 1999, pp. 5354-5361.

Simonian, A. L. et al., "FET based biosensors for the direct detection of organophosphate neurotoxins", Electroanalysis, vol. 16(22), 2004, pp. 1896-1906.

Souteyrand, E. et al., "Direct detection of the hybridization of synthetic homo-oligomer DNA sequences by field effect", J Phys Chem B, vol. 101(15), 1997, pp. 2980-2985.

Starodub, N. et al., "Immunosensor for the determination of the herbicide simazine based on an ion-selective field-effect transistor", Analytica Chimica Acta, vol. 424, 2000, pp. 37-43.

Takenaka, S. et al., "DNA Sensing on a DNA Probe-Modified Electrode Using Ferrocenylnaphthalene Dimide as the Electrochemically Active Ligand", Anal. Chem., vol. 72(6), 2000, pp. 1334-1341.

Tomaszewski, D. et al., "Electrical characterization of ISFETs", J Telecomm Info Technol, 2007, pp. 55-60.

Toumazou, C. et al., "Using transistors to linearase biochemistry", Elect Let, vol. 43(2), 2007, p. 3.

Truman, P. et al. "Monitoring liquid transport and chemical composition in lab on a chip systems using ion sensitive FET devices", Lab on a Chip, vol. 6, 2006, pp. 1220-1228.

Uslu, F. et al., "Labelfree fully electronic nucleic acid detection system based on a field-effect transistor device", Biosens & Bioelectron, vol. 19(12), 2004, pp. 1723-1731.

Van Der Wouden, E. et al., "Directional flow induced by synchronized longitudinal and zeta-potential controlling AC-electrical fields", Lab Chip, vol. 6(10), 2006, pp. 1300-1305.

Van Hal, R.E.G. et al., "A general model to describe the electrostatic potential at electrolyte oxide interfaces", Advances in Colloid and Interface Science, vol. 69, 1996, pp. 31-62.

Van Kerkhof, J. et al., "ISFET Responses on a stepwise change in electrolyte concentration at constant pH", Sensors Actuators B: Chemical, vol. 18-19, 1994, pp. 56-59.

Van Kerkhof, J. et al., "The ISFET based heparin sensor with a monolayer of protamine as affinity ligand", Biosensors & Bioelectronics, vol. 10(3), 1995, pp. 269-282.

Van Kerkhof, J., "Development of an ISFET based heparin sensor using the ion-step measuring method", Biosensors and Bioelectronics, 8 (9-10). pp. 463-472.

Wagner, T. et al., "All-in-one" solid-state device based on a light-addressable potentiometric sensor platform, Sensors and Actuators B, vol. 117, 2006, pp. 472-479.

Wang, W. et al., "Label-free detection of small-molecule-protein interactions by using nanowire nanosensors", Proc. of the Natl. Acad. of Sciences (PNAS), vol. 102(9), 2005, pp. 3208-3212.

Woias, P. et al., "Slow pH response effects of silicon nitride ISFET sensors", Sensors and Actuators B, vol. 48, 1998, pp. 501-504.

Woias, P., "Modeling the short time response of ISFET sensors", Sensors and Actuators B, vol. 24-25, 1995, pp. 211-217.

Wu, P. et al., "DNA and protein microarray printing on silicon nitride waveguide surfaces", Biosensens Bioelectron, vol. 21(7), 2006, pp. 1252-1263.

Xu, J. et al., "Analytical Aspects of FET-Based Biosensors", Frontiers in Bioscience, vol. 10, 2005, pp. 420-430.

Yeow, T.C.W. et al., "A very large integrated pH-ISFET sensor array chip compatible with standard CMOS processes", Sensor and Actuators B, vol. 44, 1997, pp. 434-440.

Yuqing, M. et al., "Ion sensitive field effect transducer-based biosensors", Biotechnology Advances, vol. 21, 2003, pp. 527-534.

Zhang, X. et al., "32-Channel Full Customized CMOS Biosensor Chip for Extracellular neural Signal Recording", Proc. of the 2nd Intl. IEEE EMBs Conf. on Neural Engineering, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", Nuc. Acids Res., vol. 29(19), e93, 2001, pp. 1-11.

\* cited by examiner

CHEMICAL SENSOR WITH SIDEWALL SPACER SENSOR SURFACE

BACKGROUND

The present disclosure relates to sensors for chemical analysis, and to methods for manufacturing such sensors.

A variety of types of chemical sensors have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

An issue that arises in the operation of large scale chemical sensor arrays is the susceptibility of the sensor output signals to noise. Specifically, the noise affects the accuracy of the downstream signal processing used to determine the characteristics of the chemical and/or biological process being detected by the sensors.

It is therefore desirable to provide devices including low noise chemical sensors, and methods for manufacturing such devices.

SUMMARY

In one implementation, a chemical sensor is described. The chemical sensor includes a chemically-sensitive field effect transistor including a floating gate conductor having an upper surface. A dielectric material defines an opening extending to the upper surface of the floating gate conductor. A conductive sidewall spacer is on a sidewall of the opening and contacts the upper surface of the floating gate conductor.

In another implementation, a method for manufacturing a chemical sensor is described. The method includes forming a chemically-sensitive field effect transistor including a floating gate conductor having an upper surface. The method further includes forming a dielectric material defining an opening extending to the upper surface of the floating gate conductor. The method further includes forming a conductive sidewall spacer on a sidewall of the opening and contacting the floating gate conductor.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

A chemical detection device is described that includes low noise chemical sensors, such as chemically-sensitive field effect transistors (chemFETs), for detecting chemical reactions within overlying, operationally associated reaction regions.

Reducing the plan or top view area (or footprint) of individual chemical sensors and the overlying reaction regions allows for higher density devices. However, as the dimensions of the chemical sensors are reduced, Applicants have found that a corresponding reduction in the sensing surface area of the sensors can significantly impact performance.

For example, for chemical sensors having sensing surfaces defined at the bottom of the reaction regions, reducing the plan view dimensions (e.g. the width or diameter) of the reaction regions results in a similar reduction in the sensing surface areas. Applicants have found that as the sensing surface area is reduced to technology limits, fluidic noise due to the random fluctuation of charge on the sensing surface contributes to an increasing proportion of the total variation in sensing surface potential. This can significantly reduce the signal-to-noise ratio (SNR) of the sensor output signal, which affects the accuracy of the downstream signal processing used to determine the characteristics of the chemical and/or biological process being detected by the sensor.

Chemical sensors described herein have sensing surface areas which are not limited to a two-dimensional area at the bottom of the reaction regions. In embodiments described herein, the sensing surface of the chemical sensor includes a generally horizontal portion along the bottom surface of the reaction region, as well as a generally vertical portion provided by a sidewall spacer on a sidewall of the reaction region.

By extending the sensing surface in a generally vertical direction, the chemical sensor can have a small footprint, while also having a sufficiently large sensing surface area to avoid the noise issues associated with small sensing surfaces. The footprint of a chemical sensor is determined in part by the width (e.g. diameter) of the overlying reaction region and can be made small, allowing for a high density array. In addition, because the sensing surface extends up the sidewall, the sensing surface area can be relatively large. As a result, low noise chemical sensors can be provided in a high density array, such that the characteristics of reactions can be accurately detected.

Figure 1:
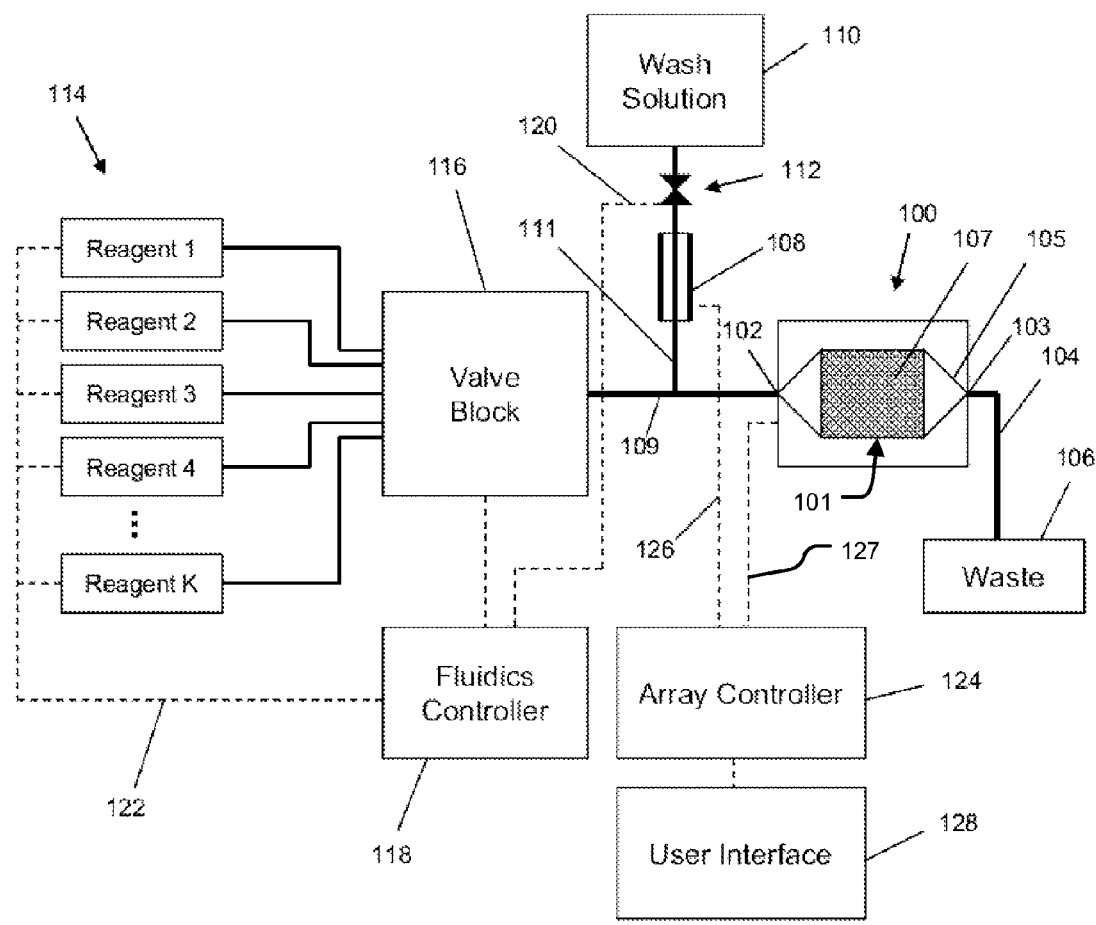
FIG. 1 illustrates a block diagram of components of a system for nucleic acid sequencing according to an exemplary embodiment.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors as described herein. The flow cell 101 includes an inlet 102, an outlet 103, and a flow chamber 105 defining a flow path of reagents over the microwell array 107.

The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes an array of reaction regions as described herein, also referred to herein as microwells, which are operationally associated with corresponding chemical sensors in the sensor array. For example, each reaction region may be coupled to a chemical sensor suitable for detecting an analyte or reaction property of interest within that reaction region. The microwell array 107 may be integrated in the integrated circuit device 100, so that the microwell array 107 and the sensor array are part of a single device or chip.

The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array. The array controller 124 also provides a reference bias voltage to the reference electrode 108 to bias the reagents 114 flowing over the microwell array 107.

During an experiment, the array controller 124 collects and processes output signals from the chemical sensors of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 1.

The values of the output signals of the chemical sensors indicate physical and/or chemical parameters of one or more reactions taking place in the corresponding reaction regions in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

The user interface 128 may display information about the flow cell 101 and the output signals received from chemical sensors in the sensor array on the integrated circuit device 100. The user interface 128 may also display instrument settings and controls, and allow a user to enter or set instrument settings and controls.

In an exemplary embodiment, during the experiment the fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors indicating chemical reactions occurring in response to the delivery of the reagents 114.

During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2:
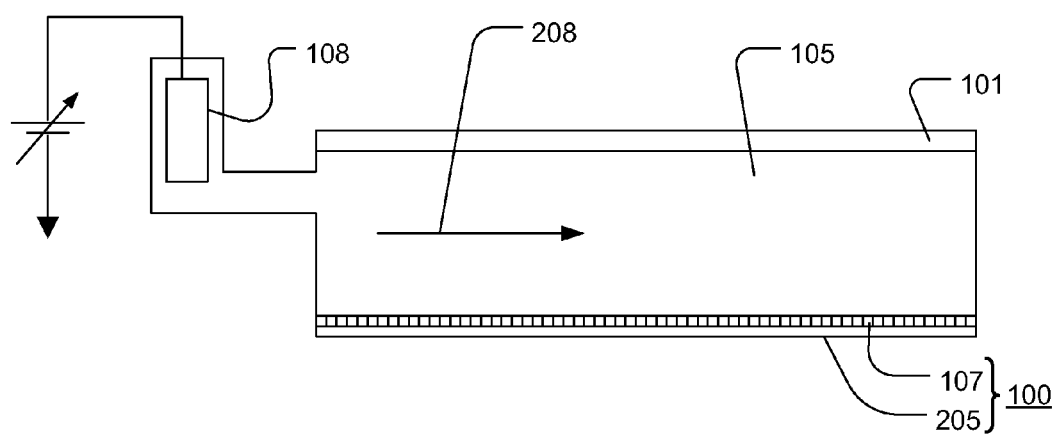
FIG. 2 illustrates a cross-sectional view of a portion of the integrated circuit device and flow cell according to an exemplary embodiment.

FIG. 2 illustrates cross-sectional and expanded views of a portion of the integrated circuit device 100 and flow cell 101. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed.

The chemical sensors of the sensor array 205 are responsive to (and generate output signals) chemical reactions within associated reaction regions in the microwell array 107 to detect an analyte or reaction property of interest. The chemical sensors of the sensor array 205 may for example be chemically sensitive field-effect transistors (chemFETs), such as ion-sensitive field effect transistors (ISFETs). Examples of chemical sensors and array configurations that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

Figure 3A:
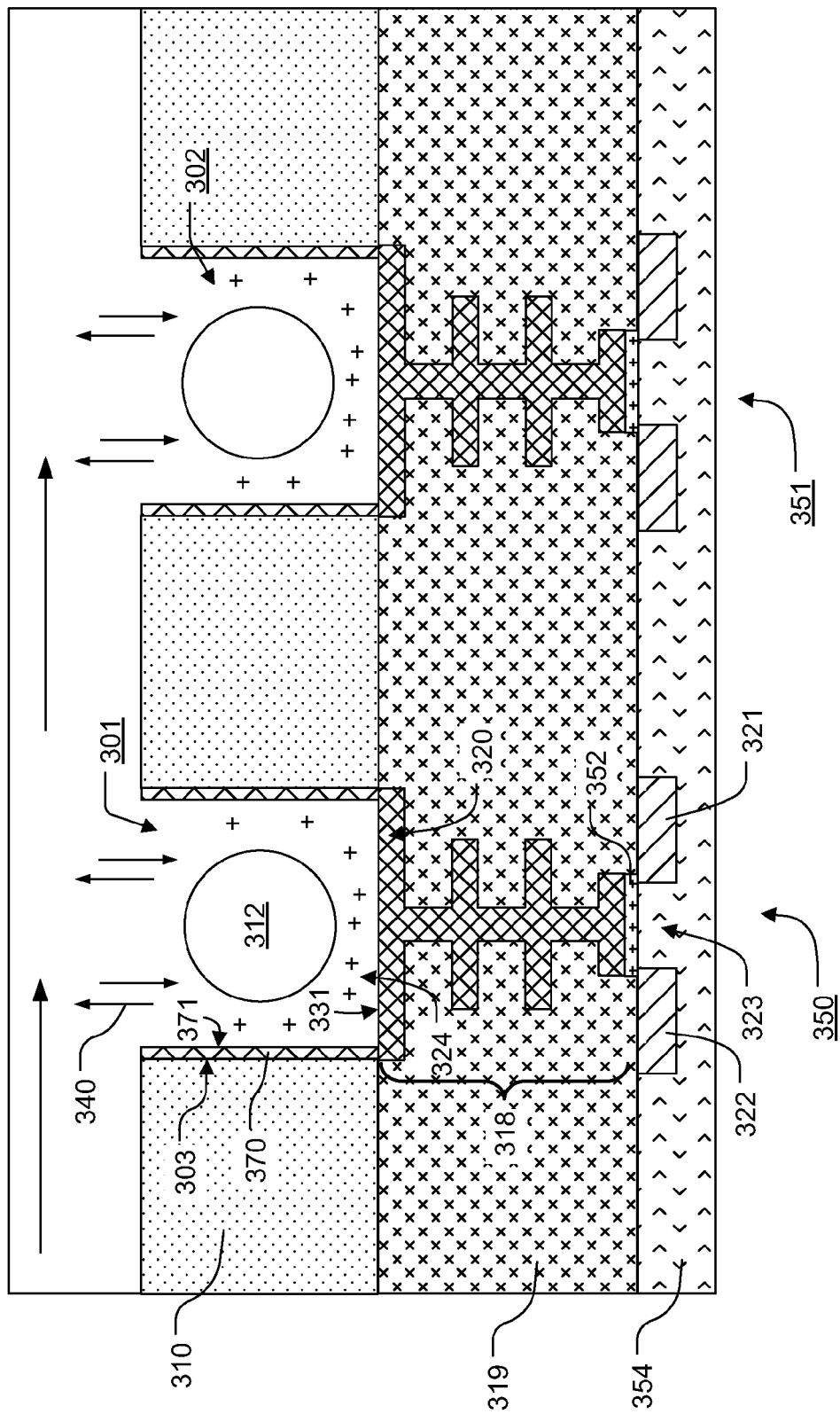
FIGS. 3A and 3B illustrate cross-sectional and plan views respectively of a representative chemical sensors and corresponding reaction regions according to an exemplary embodiment.

FIG. 3A illustrates a cross-sectional view of two representative chemical sensors and their corresponding reaction regions according to an exemplary embodiment. In FIG. 3, two chemical sensors 350, 351 are shown, representing a small portion of a sensor array that can include millions of chemical sensors.

Chemical sensor 350 is coupled to corresponding reaction region 301, and chemical sensor 351 is coupled to corresponding reaction region 302. Chemical sensor 350 is representative of the chemical sensors in the sensor array. In the illustrated example, the chemical sensor 350 is a chemically-sensitive field effect transistor (chemFET), more specifically an ion-sensitive field effect transistor (ISFET) in this example.

The chemical sensor 350 includes a floating gate structure 318 having a sensor plate 320 underlying the reaction region 301. As can be seen in FIG. 3A, the sensor plate 320 is the uppermost floating gate conductor in the floating gate structure 318. In the illustrated example, the floating gate structure 318 includes multiple patterned layers of conductive material within layers of dielectric material 319.

The chemical sensor 350 also includes a source region 321 and a drain region 322 within a semiconductor substrate 354. The source region 321 and the drain region 322 comprise doped semiconductor material have a conductivity type different from the conductivity type of the substrate 354. For example, the source region 321 and the drain region 322 may comprise doped P-type semiconductor material, and the substrate may comprise doped N-type semiconductor material.

Channel region 323 separates the source region 321 and the drain region 322. The floating gate structure 318 overlies the channel region 323, and is separated from the substrate 354 by a gate dielectric 352. The gate dielectric 352 may be for example silicon dioxide. Alternatively, other dielectrics may be used for the gate dielectric 352.

As shown in FIG. 3A, the reaction region 301 is within an opening having a sidewall 303 extending through dielectric material 310 to the upper surface 331 of the sensor plate 320. The dielectric material 310 may comprise one or more layers of material, such as silicon dioxide or silicon nitride.

The dimensions of the openings, and their pitch, can vary from implementation to implementation. In some embodiments, the openings can have a characteristic diameter, defined as the square root of 4 times the plan view cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or even not greater than 0.1 micrometers.

The chemical sensor 350 includes an electrically conductive sidewall spacer 370 on the sidewall 303 of the dielectric material 310. In the illustrated embodiment, the inner surface 371 of the conductive sidewall spacer 370 is an outer surface of the reaction region 301. In addition, the upper surface 331 of the sensor plate 320 is a bottom surface of the reaction region 301. That is, there is no intervening deposited material layer between the inner surface 371 of the conductive sidewall spacer 370 and the reaction region 301, or between the upper surface 331 of the sensor plate 320 and the reaction region 301. As a result of this structure, the upper surface 331 of the sensor plate 320 and the inner surface 371 of the conductive sidewall spacer 370 is cup-shaped and acts as the sensing surface of the chemical sensor 350. The sensor plate 320 and the sidewall spacer 370 may each comprise one or more of a variety of different materials to facilitate sensitivity to particular ions (e.g. hydrogen ions).

The cup-shaped sensing surface allows the chemical sensor 350 to have a small plan view area, while also having a sufficiently large surface area to avoid the noise issues associated with small sensing surfaces. The plan view area of the chemical sensor is determined in part by the width (or diameter) of the reaction region 301 and can be made small, allowing for a high density array. In addition, because the sensing surface extends up the sidewall 303, the sensing surface area depends upon the distance of this extension and the circumference of the reaction region 301, and can be relatively large. As a result, low noise chemical sensors 350, 351 can be provided in a high density array, such that the characteristics of reactions can be accurately detected.

During manufacturing and/or operation of the device, a thin oxide of the material of the electrically conductive sidewall spacer 370 may be grown on the inner surface 371 which acts as a sensing material (e.g. an ion-sensitive sensing material) for the chemical sensor 350. Similarly, a thin oxide of the material of the electrically conductive sensor plate 320 may be grown on the upper surface 331 which also acts as a sensing material. Whether an oxide is formed depends on the conductive materials, the manufacturing processes performed, and the conditions under which the device is operated.

In some embodiments, the sidewall spacer 370 and the upper layer of the sensor plate 320 may be the same material. For example, in one embodiment the sidewall spacer 370 and the upper layer of the sensor plate 320 may each be titanium nitride, and titanium oxide or titanium oxynitride may be grown on the inner surface 371 and the upper surface 331 during manufacturing and/or during exposure to solutions during use.

Alternatively, the sidewall spacer 370 and the upper layer of the sensor plate 320 may comprise different materials. In such a case, the upper layer of the sensor plate 320 may be a material that provides relatively high buffering of the particular ions of interest (e.g. hydrogen ions) compared to material of the sidewall spacer 370 for the given operating conditions. For example, in one embodiment in which the operational pH level of the solution is between 7 and 9, the upper layer of the sensor plate 320 is titanium nitride, while the sidewall spacer 320 is hafnium. As described in more detail below, the use of different materials for the sidewall spacer 370 and the upper layer of the sensor plate 320 can enable the SNR of the sensor output signal of the chemical sensor 350 to be maximized.

In the illustrated example, the sidewall spacer 370 and the sensor plate 320 are each shown as single layers of material. More generally, the sidewall spacer 370 and the sensor plate 320 may each comprise one or more layers of a variety of electrically conductive materials, such as metals or ceramics, depending upon the implementation. The conductive material can be for example a metallic material or alloy thereof, or can be a ceramic material, or a combination thereof. An exemplary metallic material includes one of aluminum, copper, nickel, titanium, silver, gold, platinum, hafnium, lanthanum, tantalum, tungsten, iridium, zirconium, palladium, or a combination thereof. An exemplary ceramic material includes one of titanium nitride, titanium aluminum nitride, titanium oxynitride, tantalum nitride, or a combination thereof.

In some alternative embodiments, an additional conformal sensing material (not shown) is deposited on the inner surface 371 of the conductive sidewall spacer 370 and on the upper surface 331 of the sensor plate 320. The sensing material may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the implementation.

Figure 3B:
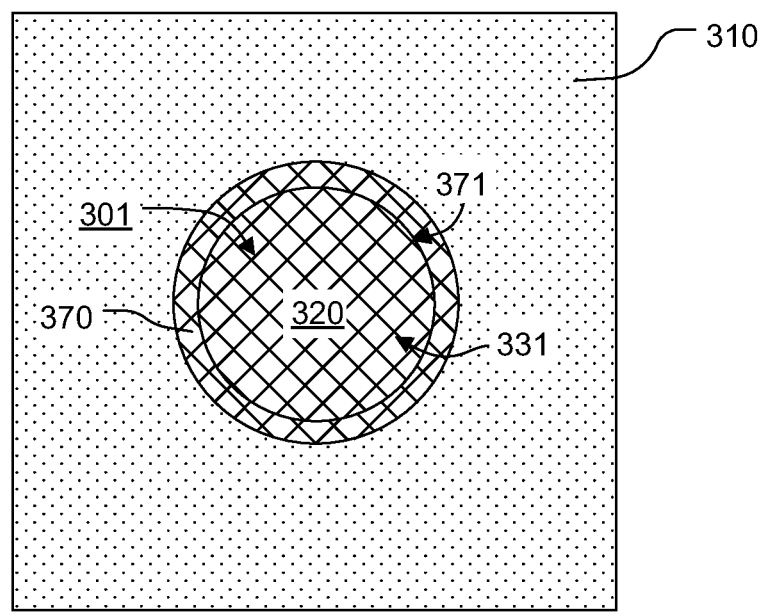

As shown in the plan view of FIG. 3B, the inner surface 371 of the sidewall spacer 370 surrounds the reaction region 301. In the illustrated example the opening and the reaction region 301 have circular cross sections. Alternatively, these may be non-circular. For example, the cross-section may be square, rectangular, hexagonal, or irregularly shaped.

Referring back to FIG. 3A, in operation, reactants, wash solutions, and other reagents may move in and out of the reaction region 301 by a diffusion mechanism 340. The chemical sensor 350 is responsive to (and generates an output signal related to) the amount of a charge 324 proximate to the sidewall spacer 370 and the sensor plate 320. The presence of charge 324 in an analyte solution alters the surface potential at the interface between the analyte solution and the sidewall spacer 370/sensor plate 320, due to the protonation or deprotonation of surface charge groups caused by the ions present in the analyte solution. Changes in the charge 324 cause changes in the voltage on the floating gate structure 318, which in turn changes in the threshold voltage of the transistor of the chemical sensor 350. This change in threshold voltage can be measured by measuring the current in the channel region 323 between the source region 321 and a drain region 322. As a result, the chemical sensor 350 can be used directly to provide a current-based output signal on an array line connected to the source region 321 or drain region 322, or indirectly with additional circuitry to provide a voltage-based output signal.

The amplitude of the desired signal detected in response to the charge 324 is a superposition of the interface between the analyte solution and the sidewall spacer 370, and the interface between the analyte solution and the sensor plate 320. Because the charge is more highly concentrated near the bottom of the reaction region 301, in some embodiments the material for the sensor plate 320 is chosen which has a relatively high buffering capacity for the particular ions of interest (e.g. hydrogen ions) for the given operating conditions. In doing so, the sensor plate 320 can maximally detect signal from an area of high charge concentration.

The buffering capacity of the material of the sidewall spacer 370 is a tradeoff between the amplitude of the desired signal detected in response to the charge 324, and the fluidic noise due to random fluctuation of charge at the interface between the analyte solution and the sidewall spacer 370/sensor plate 320. A relatively high buffering material for the sidewall spacer 370 increases the effective fluidic interface area for the chemical sensor 350, which reduces the fluidic noise. However, since the surface density of the charge 324 decreases with distance from the bottom of the reaction region, the high buffering material detects a greater proportion of the signal from areas having lower charge concentration, which can reduce the overall amplitude of the desired signal detected by the sensor 350. In contrast, a relatively low buffering material for the sidewall spacer 370 reduces the effective sensing surface area and thus increases the fluidic noise, but also increases the overall amplitude of the desired signal detected by the sensor 350 due to a greater proportion of the signal being contributed by the sensor plate 320.

For a very small sensing surface area, Applicants have found that the fluidic noise changes as a function of the sensing surface area differently than the amplitude of the desired signal. Because the SNR of the sensor output signal is the ratio of these two quantities, there is an optimal material for the sidewall spacer 370 having buffering characteristics at which SNR is maximum.

The material having the optimal buffering capacity for the sidewall spacer 370 can vary from embodiment to embodiment depending on the material characteristics of the sensor plate 320, the volume, shape, aspect ratio (such as base width-to-well depth ratio), and other dimensional characteristics of the reaction regions, the nature of the reaction taking place, as well as the reagents, byproducts, or labeling techniques (if any) that are employed. The optimal material may for example be determined empirically.

In an embodiment, reactions carried out in the reaction region 301 can be analytical reactions to identify or determine characteristics or properties of an analyte of interest. Such reactions can generate directly or indirectly byproducts that affect the amount of charge adjacent to the sensor plate 320 and the sidewall spacer 370. If such byproducts are produced in small amounts or rapidly decay or react with other constituents, multiple copies of the same analyte may be analyzed in the reaction region 301 at the same time in order to increase the output signal generated. In an embodiment, multiple copies of an analyte may be attached to a solid phase support 312, either before or after deposition into the reaction region 301. The solid phase support 312 may be microparticles, nanoparticles, beads, solid or porous comprising gels, or the like. For simplicity and ease of explanation, solid phase support 312 is also referred herein as a particle. For a nucleic acid analyte, multiple, connected copies may be made by rolling circle amplification (RCA), exponential RCA, or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

FIGS. 4 to 7 illustrate stages in a manufacturing process for forming an array of chemical sensors and corresponding well structures according to an exemplary embodiment.

Figure 4:
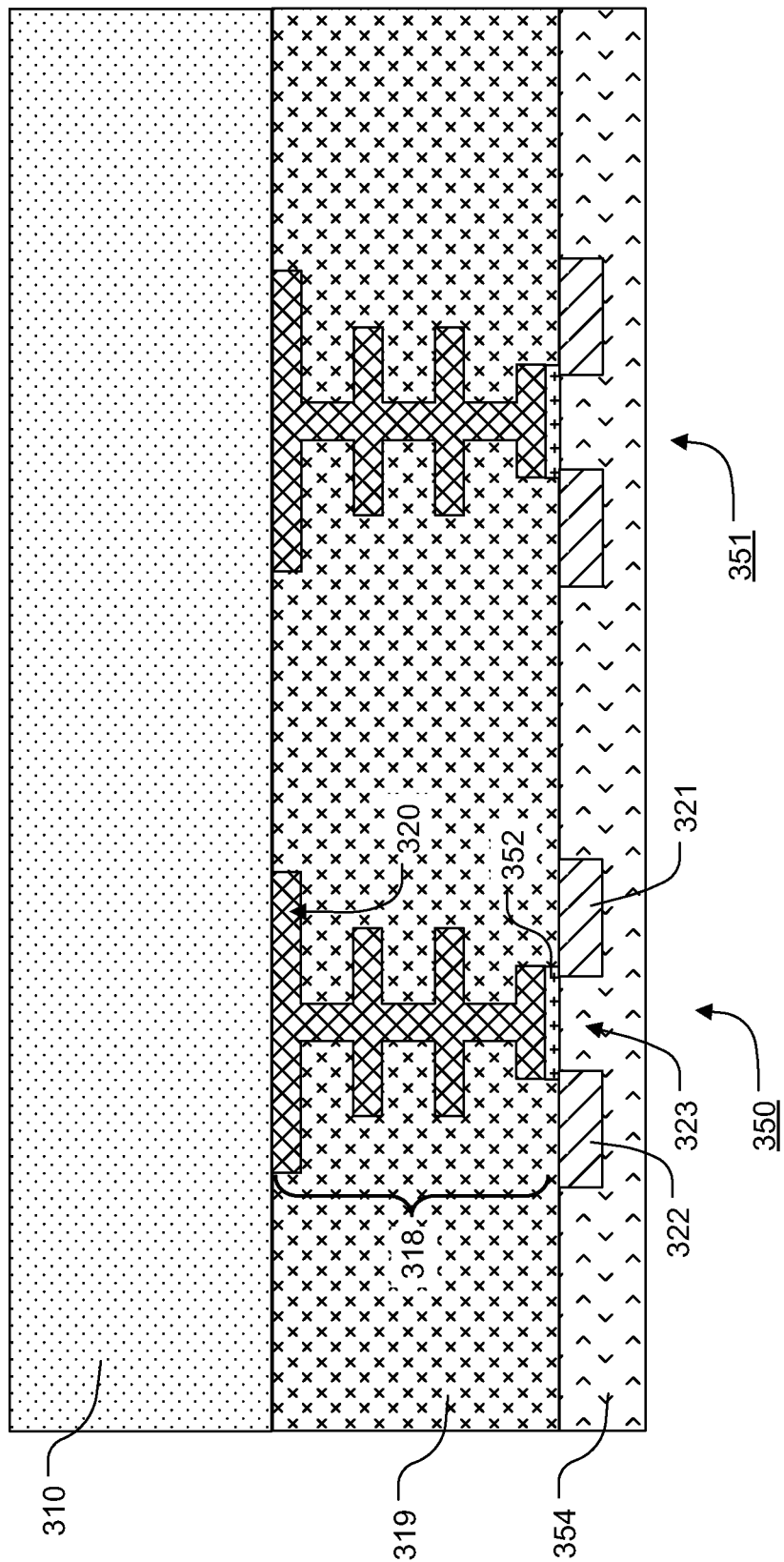
FIGS. 4 to 7 illustrate stages in a manufacturing process for forming an array of chemical sensors and corresponding well structures according to an exemplary embodiment.

FIG. 4 illustrates a first stage of forming a structure including a dielectric material 310 on the sensor plate 320 of the field effect transistor of the chemical sensor 350. The structure in FIG. 4 can be formed by depositing a layer of gate dielectric material on the semiconductor substrate 354, and depositing a layer of polysilicon (or other electrically conductive material) on the layer of gate dielectric material. The layer of polysilicon and the layer gate dielectric material can then be etched using an etch mask to form the gate dielectric elements (e.g. gate dielectric 352) and the lowermost conductive material element of the floating gate structures. Following formation of an ion-implantation mask, ion implantation can then be performed to form the source and drain regions (e.g. source region 321 and a drain region 322) of the chemical sensors.

A first layer of the dielectric material 319 can then be deposited over the lowermost conductive material elements. Conductive plugs can then be formed within vias etched in the first layer of dielectric material 319 to contact the lowermost conductive material elements of the floating gate structures. A layer of conductive material can then be deposited on the first layer of the dielectric material 319 and patterned to form second conductive material elements electrically connected to the conductive plugs. This process can then be repeated multiple times to form the completed floating gate structure 318 shown in FIG. 4. Alternatively, other and/or additional techniques may be performed to form the structure.

Forming the structure in FIG. 4 can also include forming additional elements such as array lines (e.g. word lines, bit lines, etc.) for accessing the chemical sensors, additional doped regions in the substrate 354, and other circuitry (e.g. access circuitry, bias circuitry etc.) used to operate the chemical sensors, depending upon the device and array configuration in which the chemical sensors described herein are implemented. In some embodiments, the elements of the structure may for example be manufactured using techniques described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

Figure 5:
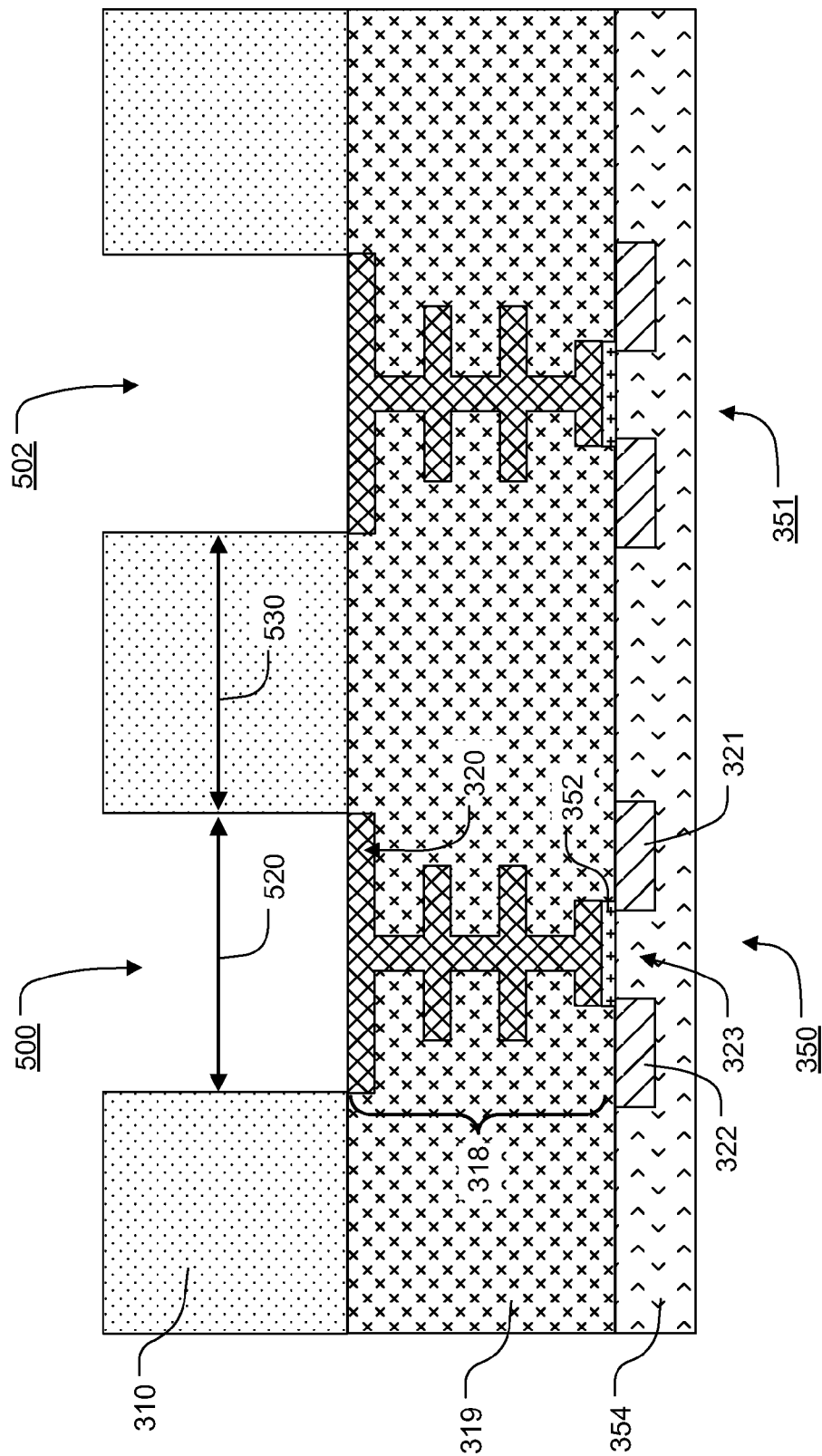

Next, the dielectric material 310 of the structure in FIG. 4 is etched to form openings 500, 502 extending to the upper surfaces of the floating gate structures of the chemical sensors 350, 351, resulting in the structure illustrated in FIG. 5.

The openings 500, 502 may for example be formed by using a lithographic process to pattern a layer of photoresist on the dielectric material 310 to define the locations of the openings 500, 502, and then anisotropically etching the dielectric material 310 using the patterned photoresist as an etch mask. The anisotropic etching of the dielectric material 310 may for example be a dry etch process, such as a fluorine based Reactive Ion Etching (RIE) process.

In the illustrated embodiment, the openings 500, 502 are separated by a distance that 530 that is equal to their width 520. Alternatively, the separation distance 530 between adjacent openings may be less than the width 520. For example, the separation distance 530 may be a minimum feature size for the process (e.g. a lithographic process) used to form the openings 500, 502. In such a case, the distance 530 may be significantly less than the width 520.

Figure 6:
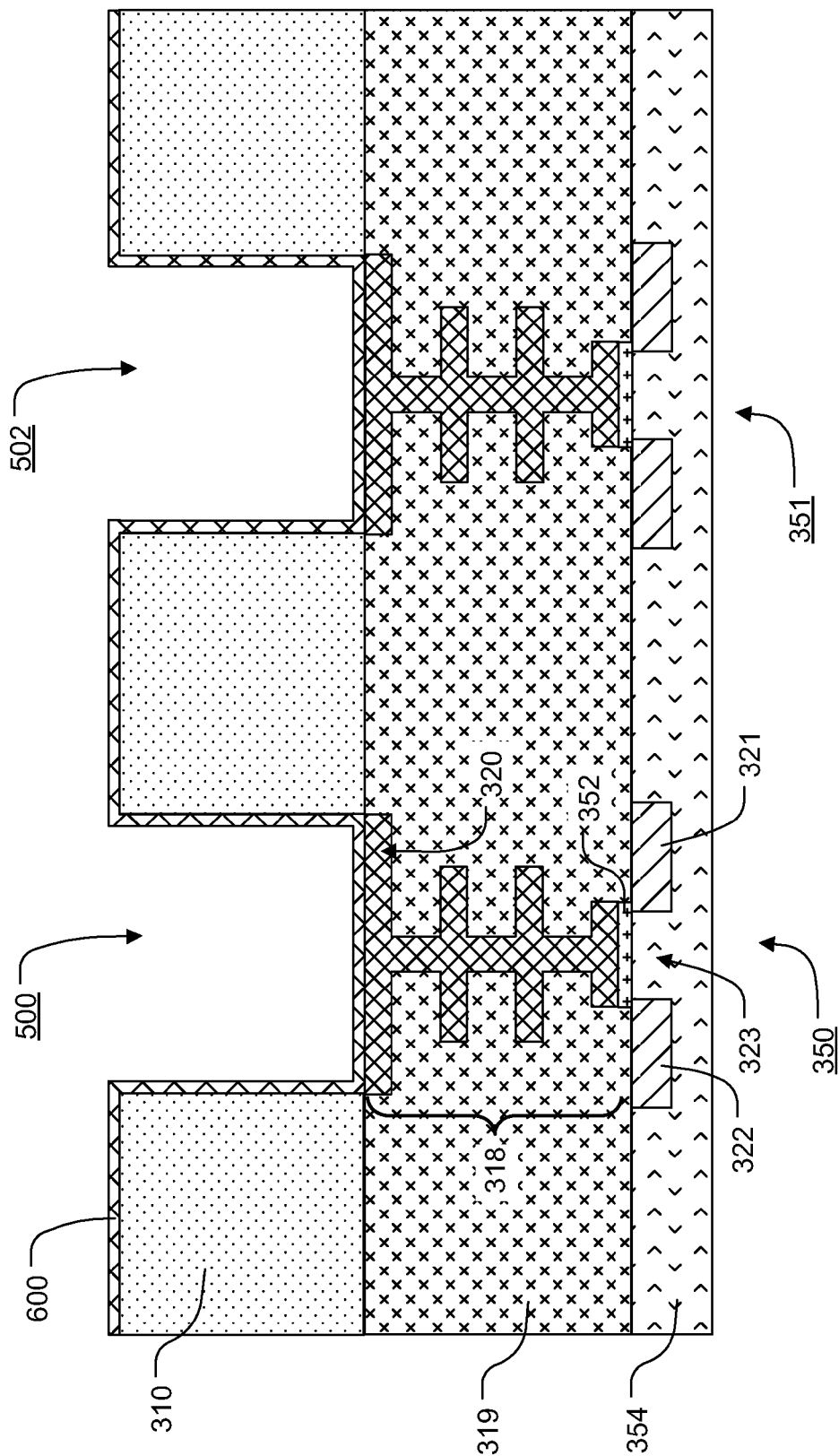

Next, a conformal layer of conductive material 600 is deposited on the structure illustrated in FIG. 5, resulting in the structure illustrated in FIG. 6. The conductive material 600 comprises one or more layers of electrically conductive material. For example, the conductive material 500 may be a layer of titanium nitride, or a layer of titanium. Alternatively, other and/or additional conductive materials may be used, such as those described above with reference to the sidewall spacer 370. In addition, more than one layer of conductive material may be deposited.

The conductive material 600 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD) etc.

Figure 7:
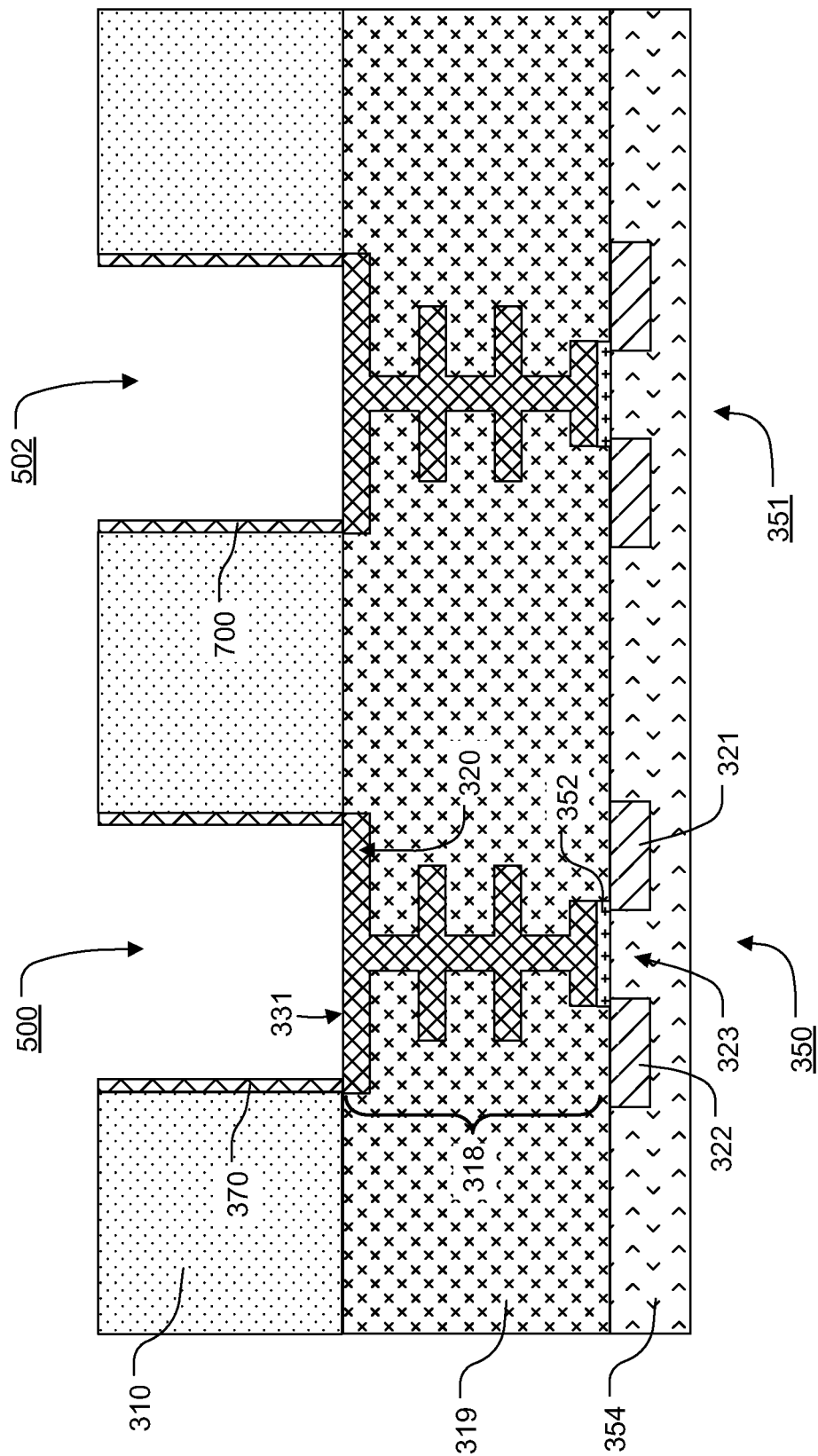

Next, an anisotropic etching process is performed on the conductive material 600 illustrated in FIG. 6 to form sidewall spacers 370, 700 within the openings 500, 502, resulting in the structure illustrated in FIG. 7. The anisotropic etching process removes the material of the layer of conductive material 600 on horizontal surfaces at a faster rate than material on vertical surfaces. In doing so, the anisotropic etching process exposes the upper surface 331 of the sensor plate 320, as well as the upper surface of the dielectric material 310. The anisotropic etching process may for example be performed using a RIE or other plasma etching process. Alternatively, other etching processes may be used.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A chemical sensor comprising:
a chemically-sensitive field effect transistor including a floating gate conductor having an upper surface;
a dielectric material defining an opening extending to the upper surface of the floating gate conductor; and
a conductive sidewall spacer on a sidewall of the opening and contacting the upper surface of the floating gate conductor; wherein the chemically-sensitive field effect transistor includes a floating gate structure comprising a plurality of conductors electrically coupled to one another and separated by dielectric layers, and the floating gate conductor is an uppermost conductor in the plurality of conductors.

2. The chemical sensor of claim 1, wherein the conductive sidewall spacer includes an inner surface surrounding a reaction region for the chemical sensor.

3. The chemical sensor of claim 1, wherein the conductive sidewall spacer comprises an electrically conductive material, and an inner surface of the conductive sidewall spacer includes an oxide of the electrically conductive material.

4. The chemical sensor of claim 1, wherein a sensing surface for the chemical sensor includes an inner surface of the conductive sidewall spacer and the upper surface of the floating gate conductor.

5. The chemical sensor of claim 1, wherein the conductive sidewall spacer comprises material different from material at the upper surface of the floating gate conductor.

6. The chemical sensor of claim 1, wherein the chemically-sensitive field effect transistor generates a sensor signal in response to a chemical reaction occurring proximate to the conductive sidewall spacer.

7. The chemical sensor of claim 1, further comprising a microfluidic structure in fluid flow communication with the chemically-sensitive field effect transistor, and arranged to deliver analytes for sequencing.

8. The chemical sensor of claim 2, wherein the inner surface of the conductive sidewall spacer is an outer surface of the reaction region, and the upper surface of the floating gate conductor is a bottom surface of the reaction region.

9. The chemical sensor of claim 4, wherein the sensing surface is sensitive to hydrogen ions.

10. The chemical sensor of claim 6, wherein the chemical reaction is a sequencing reaction.

* * * * *